United States Patent
Sliski et al.

(10) Patent No.: US 7,758,241 B2
(45) Date of Patent: *Jul. 20, 2010

(54) HIGHLY SHIELDED RADIATION THERAPY SYSTEM

(76) Inventors: Alan P. Sliski, 273 Concord Rd., Lincoln, MA (US) 01773; Jason Koshnitsky, 44 Carter Dr., Framingham, MA (US) 01701

( * ) Notice: Subject to any disclaimer, the term of this patent is extended or adjusted under 35 U.S.C. 154(b) by 0 days.

This patent is subject to a terminal disclaimer.

(21) Appl. No.: 12/259,005

(22) Filed: Oct. 27, 2008

(65) Prior Publication Data

US 2009/0110146 A1   Apr. 30, 2009

Related U.S. Application Data

(60) Provisional application No. 60/983,208, filed on Oct. 28, 2007.

(51) Int. Cl.
 *H01J 35/16* (2006.01)
(52) U.S. Cl. .................................... 378/203; 250/505.1
(58) Field of Classification Search .................. 378/65, 378/203, 145; 250/505.1, 515.1
See application file for complete search history.

(56) References Cited

U.S. PATENT DOCUMENTS

| | | | |
|---|---|---|---|
| 5,289,520 A | 2/1994 | Pellegrino et al. | |
| 5,564,438 A | 10/1996 | Merchant | |
| 6,325,538 B1 * | 12/2001 | Heesch | 378/203 |
| 6,448,571 B1 * | 9/2002 | Goldstein | 250/515.1 |
| 7,526,066 B2 * | 4/2009 | Koshnitsky et al. | 378/68 |
| 2002/0156365 A1 | 10/2002 | Tsekos | |
| 2004/0041107 A1 | 3/2004 | Cadwalader et al. | |
| 2005/0218348 A1 | 10/2005 | Fehrenbacher et al. | |
| 2007/0018111 A1 | 1/2007 | Calderon et al. | |
| 2007/0033735 A1 | 2/2007 | Formenti | |
| 2007/0064867 A1 | 3/2007 | Hansen et al. | |
| 2007/0206203 A1 | 9/2007 | Trainer | |
| 2007/0211854 A1 | 9/2007 | Koshnitsky et al. | |
| 2009/0064413 A1 | 3/2009 | Sliski et al. | |

OTHER PUBLICATIONS

International Search Report dated Apr. 12, 2008, issued in corresponding International Application No. PCT/US2008/075421.
International Search Report dated Dec. 24, 2008, issued in corresponding International Application No. PCT/US2008/081329.
Goodman, Karyn A. et al., "Dosimetric Analysis of a Simplified Intensity Modulation Technique for Prone Breast Radiotherapy," Int. J. Radiation Oncology Biol. vol. 60, No. 1, pp. 95-102, 2004.
"Prone Breast System." Bionix Radiation Therapy. Jun. 12, 2009 <www.bionix.com/Images/ProneBreast.pdf>.
"Prone Breast Patient Positioning." CDR Systems. Jun. 12, 2009 <www.cdrsys.ca/breast/>.
"Horizon Prone Breastboard." Civco Medical Solutions. Jun. 12, 2009 <http://civco.com/oncology/bt-positioning/horizonprone/>.

\* cited by examiner

*Primary Examiner*—Courtney Thomas

(57) ABSTRACT

A shielding system which can be applied to a radiation therapy system and/or diagnostic system includes a scatter shield configured to absorb scattered radiation from a patient, a source shield to absorb unwanted radiation from the radiation source, and an anti-reflective beam dump configured to absorb radiation that is transmitted through a patient. The radiation therapy and/or diagnostic system includes a radiation source positioned in the source shield, and a patient support positioned in the scatter shield.

17 Claims, 1 Drawing Sheet

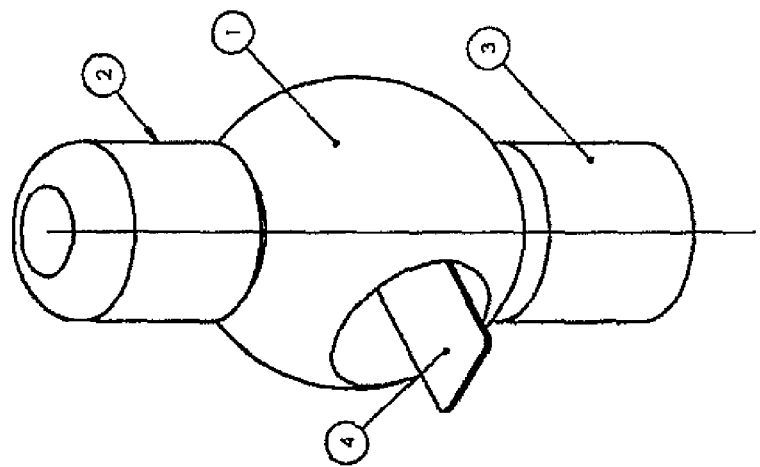
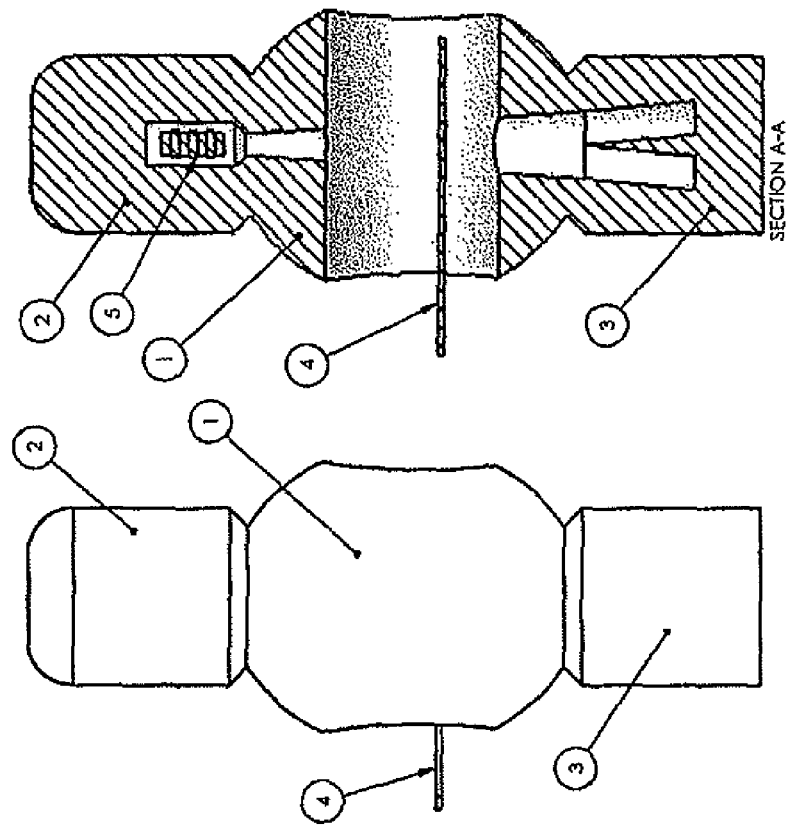
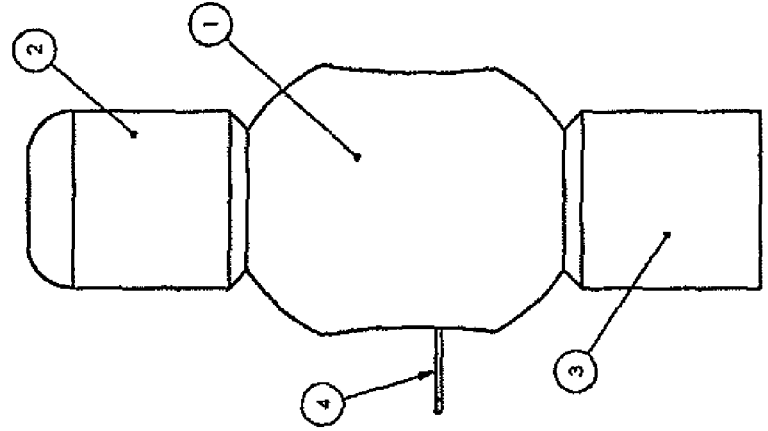
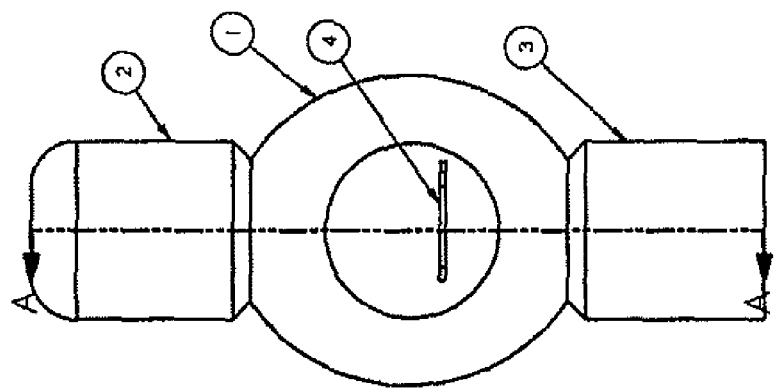

HIGHLY SHIELDED RADIATION THERAPY SYSTEM

RELATED APPLICATIONS

This application claims the benefit of U. S. Provisional Application Ser. No. 60/983,208, filed Oct. 28, 2007, the contents of which are incorporated herein by reference, in their entirety.

BACKGROUND OF THE INVENTION

In the field of radiation therapy, high energy radiation is used to deliver a therapeutic dose to targets within the body to treat cancer. The machines that generate and deliver the radiation produce beams from a source that rotates around the patient. Stray radiation from several sources must be shielded by a thick-walled room or bunker so as to not affect nearby workers and the public. The three main sources of stray radiation that must be shielded are stray radiation from the radiation source and associated beam-shaping elements, scatter from the patient, and the remainder of the beam that travels through the patient.

The shielding of the radiation source is done within the machine, but a significant fraction still escapes. The leakage radiation from a standard linear accelerator must be below 0.1% to meet regulatory requirements. This is still too intense to allow out of the treatment room.

Scatter from the patient as the beam transits the tissue before, including and after the target volume is also significant, but of lower effective energy. This source is also considered separately in calculating the shielding requirements of the bunker.

The most intense source of stray radiation during a treatment is the direct treatment beam that exits the patient after delivering dose to the path of the radiation in the body. Some treatment machines have been supplied with a beam stop that absorbs a large fraction of this direct beam. The beam stop is often used as a counterweight for the shielded rotating radiation source. It is generally designed to absorb as much of the beam as possible given the weight required to balance the radiation source. Scatter from the beam stop also contributes to stray radiation within the treatment room. A typical thickness of lead, for example required to attenuate a high energy photon beam by a factor of ten (a tenth-value layer or TVL) is 5.7 cm. An 18 cm thick lead beam stop reduces the beam intensity by a factor of 1000. The resulting transmission through this beam stop still exceeds the dose rate limit for occupational exposure given a typical workload for the therapy machine.

The bunker that contains the treatment machine is generally a distinctly different part of the whole installation. It is designed to house the treatment machine by trained medical physicists certified in shielding design, and built as an architectural structure of the building, usually underground or at ground level. The bunker walls are typically 2-3.5 meters thick and made of concrete. The additional cost of the bunker constitutes a significant fraction of the total installed cost of the system, and requires a large footprint in the building to accommodate the treatment machine and bunker. This arrangement of radiation source and bunker is a result of existing machines using an open beam to be able to treat any area of the body. The typical radiation therapy system sold today is optimized for treating deep-seated tumors near critical structures.

SUMMARY OF THE INVENTION

The present invention is directed to a self-shielding system for absorbing radiation which eliminates the need for a bunker.

According to one aspect of the invention, a self-shielded therapy and/or diagnostic machine, which is formed specifically to lower an unwanted dose of radiation to a patient and surrounding areas, can offer benefits for the patient, workers, and the overall cost of delivering radiation therapy by eliminating much or all of the traditional shielded bunker built to house machines with open beams.

According to one aspect of the invention, the present invention is directed to the optimization of machine and patient positioning geometry to allow substantial reduction in stray radiation that escapes the system.

The present invention is directed to a shielding system for a radiation therapy and/or diagnostic system which includes a scatter shield configured to absorb scattered radiation from a patient, a source shield on the scatter shield configured to absorb unwanted radiation from a radiation source and beam shaping elements, and an anti-reflective beam dump below the scatter shield configured to absorb radiation that is transmitted through a patient.

In one embodiment, the shielding system includes shielding for primary, exit, and scattered radiation such that leakage radiation is below 0.02 mSv/week for a workload of 1000 Gy/week at isocenter when using the methods contained in NCRP report 151 for calculating and measuring the external dose rate. In another embodiment, the shielding system includes highly shielded zone is produced for at least an area adjacent to the machine sufficient to house an operator console.

In one embodiment, the shielding system includes full shielding for primary and scattered radiation such that leakage radiation is below 0.1 mSv/week at the operator's location for a workload of 1000 Gy/week at isocenter when using the methods contained in NCRP report 151 for calculating and measuring the external dose rate.

In one embodiment, the shielding system includes in-room shielding for an operator.

In accordance with another aspect of the invention, the present invention is directed to a radiation therapy system for treating a patient which includes a radiation source configured to produce a radiation beam, a patient support system, a shielding system surrounding the radiation source and at least a portion of the patient support system, wherein the shielding system absorbs stray radiation, and a patient positioning system for positioning the patient in the shielding system.

In one embodiment, the shielding system includes shielding for primary, exit, and scattered radiation such that leakage radiation is below 0.02 mSv/week for a workload of 1000 Gy/week at isocenter when using the methods contained in NCRP report 151 for calculating and measuring the external dose rate. In another embodiment, a highly shielded zone is produced for at least an area adjacent to the machine sufficient to house an operator console.

In one embodiment, the shielding system includes full shielding for primary and scattered radiation such that leakage radiation is below 0.1 mSv/week at the operator's location for a workload of 1000 Gy/week at isocenter when using the methods contained in NCRP report 151 for calculating and measuring the external dose rate.

In one embodiment, the radiation source is a linear accelerator.

In another embodiment, the shielding system includes full shielding for primary and scattered radiation such that leakage radiation is below 0.02 mSv/week at 2 meters from the surface of the radiation therapy system for a workload of 1000 Gy/week at isocenter when using the methods contained in NCRP report 151 for calculating and measuring the external dose rate.

In another embodiment, the shielding system includes full shielding for primary and scattered radiation such that leakage radiation is below 0.1 mSv/week at 2 meters from the surface of the radiation therapy system for a workload of 1000 Gy/week at isocenter when using the methods contained in NCRP report 151 for calculating and measuring the external dose rate.

In another embodiment, the shielding system includes primary shielding which is better than 0.001% of the primary beam dose rate.

In another embodiment, the radiation therapy system further includes in-room shielding for an operator.

In one embodiment, the radiation therapy system further includes in-room shielding for an operator.

In one embodiment, the shielding system includes a scatter shield configured to absorb scattered radiation from a patient positioned on the patient support system.

In one embodiment, the shielding system comprises a source shield in which the radiation source is positioned.

In one embodiment, the shielding system includes an anti-reflective beam dump positioned to absorb the beam transmitted through the patient and to reduce backscatter onto the patient.

In one embodiment the patient support system includes a patient interface surface and an aperture configured to permit passage of a patient anatomy to be treated through the patient interface surface.

In accordance with another aspect of the invention, the invention is directed to a radiation therapy system for treating a patient which includes a shielding system including a scatter shield configured to absorb scattered radiation from a patient, a source shield on the scatter shield configured to absorb unwanted radiation from a radiation source and beam shaping elements, and an anti-reflective beam dump below the scatter shield configured to absorb radiation that is transmitted through a patient. The radiation therapy system further includes a radiation source positioned in the source shield, and a patient support positioned in the scatter shield.

In one embodiment, the radiation source is a linear accelerator. In another embodiment, the shielding system includes full shielding for primary and scattered radiation such that leakage radiation is below 0.02 mSv/week at 2 meters from the surface of the radiation therapy system for a workload of 1000 Gy/week at isocenter when using the methods contained in NCRP report 151 for calculating and measuring the external dose rate. In another embodiment, the shielding system includes full shielding for primary and scattered radiation such that leakage radiation is below 0.1 mSv/week at 2 meters from the surface of the radiation therapy system for a workload of 1000 Gy/week at isocenter when using the methods contained in NCRP report 151 for calculating and measuring the external dose rate. In another embodiment, the shielding system includes primary shielding which is better than 0.001% of the primary beam dose rate. In another embodiment, the radiation therapy system further includes in-room shielding for an operator.

In one embodiment, the shielding system includes shielding for primary and scattered radiation such that leakage radiation is below 0.02 mSv/week at the operator's position for a workload of 1000 Gy/week at isocenter when using the methods contained in NCRP report 151 for calculating and measuring the external dose rate.

In one embodiment, the shielding system includes full shielding for primary and scattered radiation such that leakage radiation is below 0.1 mSv/week at the operator's position for a workload of 1000 Gy/week at isocenter when using the methods contained in NCRP report 151 for calculating and measuring the external dose rate.

In one embodiment, the radiation therapy system further includes in-room shielding for an operator.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a front view of a therapy system according to an embodiment of the present invention.

FIG. 2 is a side view of the therapy system of FIG. 1.

FIG. 3 is a cross-sectional view of the therapy system of FIG. 1.

FIG. 4 is an isometric view of the therapy system of FIG. 1.

DETAILED DESCRIPTION OF THE INVENTION

The present invention is directed to a self-shielding system for absorbing radiation. The self-shielding system eliminates the need for radiation therapy and/or diagnostic systems to be shielded in a thick-walled room or bunker. The self-shielding system according to the present invention absorbs substantially all of the three main sources of stray radiation, i.e., stray radiation from a radiation source and associated beam-shaping elements, scatter from a patient, and the remainder of the beam that is transmitted through the patient, such that the regulatory requirements for leakage radiation are met.

The self-shielding system according to the present invention, as illustrated in FIGS. 1-4, includes a source shield 2 which absorbs stray radiation from a radiation source and associated beam-shaping elements. The self-shielding system according to the present invention further includes a scatter shield 1 which absorbs scatter from a patient. In addition, the self-shielding system according to the present invention includes an anti-reflective beam dump 3 which absorbs the remainder of the beam that is transmitted through the patient. The source shield 2, the scatter shield 1 and anti-reflective beam dump 3, in combination, limit the leakage radiation from the self-shielding system to at least the regulatory requirements. Thus, the self-shielding system including the source shield 2, the scatter shield 1 and anti-reflective beam dump 3 according to the present invention need not be shielded by a thick-walled room or bunker, reducing costs and increasing versatility.

The self-shielding system of the present invention can be applied to radiation therapy systems and/or diagnostic systems or any other application in order to reduce stray radiation.

Throughout the following description, the self-shielding system of the invention is described in connection with an exemplary radiation therapy and/or diagnostic system. However, it is noted that the self-shielding system of the invention can be applied to any radiation system. Specifically, the self-shielding system can be applied to any radiation therapy and/or diagnostic system.

An exemplary radiation therapy and/or diagnostic system to which the self-shielding system of the present invention is applicable is described in U.S. patent application Ser. No. 11/530,124, filed Sep. 8, 2006, the contents of which are incorporated herein by reference in their entirety. The therapy system includes a substantially horizontal table with an aperture that is provided for the patient to lie on in a prone position. The breast or extremity to be treated is positioned through the aperture for alignment and treatment. In this position, gravity is an assist in elongating the breast and maximizing the separation between the target volume and the critical structures within the patient such as the chest wall, lung, and heart. According to the present invention, by making the table from a shielding material, the unwanted dose from stray radiation to the rest of the patient can be greatly reduced or eliminated. The structure of the radiation source assembly below the table in this embodiment can be self-shielding. According to the present invention, a sufficient thickness of shielding material surrounds the radiation source, beam shaping elements that scatter radiation, and the beam stop to reduce the leakage radiation dose to levels required outside shielded rooms for traditional machines with an open beam.

An embodiment of the present invention is directed to devices and methods for delivering an accurately located dose of radiation to a predetermined target volume within an anatomical site, while also incorporating an integrated self-shielding system into the radiation producing system. The following description and FIGS. 1-4 illustrate a machine configuration where the radiation source and shield assembly are rotating and moveable. The other case, where the patient may rotate with respect to the source assembly is geometrically equivalent to the rotating radiation source assembly FIG. 1 illustrates the basic elements of a radiation therapy system to which the invention is applicable. Source shield 2 shields the stray radiation from the source 5 and scattered radiation from a beam modulator or a collimator, as illustrated in FIG. 3. Scatter shield 1 absorbs scattered radiation from the patient who is positioned on a patient table 4. The scatter shield 1 includes an aperture through which the patient is positioned within the scatter shield 1. Beam dump 3 absorbs the beam that is transmitted through the patient and is also configured to reduce backscatter onto the patient and through the patient aperture. In one embodiment, the patient table 4 is a substantially horizontal table with an aperture that is provided for the patient to lie on in a prone position. The breast or extremity to be treated is positioned through the aperture for alignment and treatment. In this position, gravity is an assist in elongating the breast and maximizing the separation between the target volume and the critical structures within the patient such as the chest wall, lung, and heart. This embodiment is one example of a fully shielded machine intended for use in treating breast cancer, but it illustrates the principles involved in a fully shielded machine according to the present invention for other anatomical sites. The patient table 4 may be any patient support. The radiation source 5, illustrated in FIG. 3, resides in the source shield 2 and emits a programmable beam of radiation through a beam modulator to deliver a dose of radiation to a target within the patient. The entire source assembly, including the shielding system, i.e., scatter shield 1, source shield 2, and anti-reflective beam dump 3, along with the radiation source 5, rotates about a vertical axis, moves along a horizontal axis and delivers radiation to the target volume within the patient resting on patient table 4. The entire assembly absorbs substantially all of the radiation produced by the source 5 and much of the scattered radiation produced by the interaction of the radiation beam with the patient.

The scatter shield 1 absorbs the scattered radiation from the patient who is positioned on the patient table 4. The source shield 2 shields the stray radiation from the source 5 and scattered radiation from a beam modulator or a collimator. The beam dump 3 absorbs the portion of the beam that is transmitted through the patient and is also configured to reduce backscatter onto the patient and through the patient aperture.

The radiation source assembly rotates on a substantially horizontal axis via rotational bearings and drive means. The patient table translates in three Cartesian axes plus up to three rotations to align the patient in the desired manner with respect to the programmable, shaped treatment beam in order to deliver the desired dose to the treatment volume while minimizing the dose to the adjacent non-target areas. FIG. 2 is a side view of the radiation therapy system of FIG. 1. FIG. 3 is a cross-sectional view of the system of FIG. 1. FIG. 4 is an isometric view of the radiation therapy system of FIG. 1. In one embodiment of the present invention, additional radiation shields positioned to provide patient access while shielding any residual scattered radiation from the system and patient may be employed.

The self-shielding system as described herein including the scatter shield 1, source shield 2 and beam dump 3 may be applied to the radiation therapy and/or diagnostic systems of U.S. patent application Ser. No. 11/530,124, filed Sep. 8, 2006, the contents of which are incorporated herein by reference in their entirety, and U.S. patent application Ser. No. 12/205,418, filed Sep. 5, 2008, the contents of which are incorporated herein by reference in their entirety, or any other radiation applications.

Any source of radiation can be accommodated as part of a radiation therapy and/or diagnostic system including the self-shielding system. Depending on the intended application, different sources of radiation may be used. For example, the energy required to treat small volumes such as the breast or other extremities is lower than a general purpose machine designed to treat target volumes deep in a large patient's abdomen. A compact LINAC, proton- or ion-beam accelerator, cobalt 60 isotopic source, or ortho- or supervoltage x-ray generator may be employed, depending on the clinician's preference for dose delivery. Lower-energy, simpler systems may be preferred in remote areas where maintenance is limited.

In one aspect, the system to which the invention applies employs at least one rotational element. The radiation source or the patient positioner can be rotated about an axis. In the case of a configuration employing a rotating radiation source, the rotating element may also include optional imaging means for localizing the target volume in situ at the time of treatment. This embodiment may include only the patient positioning and radiation source systems, or also employ imaging means. If the therapy radiation source can also produce diagnostic energy and quality beams, only one radiation source is required if x-ray imaging is desired. The imaging system can be optical or use ionizing radiation. In one configuration, a high energy portal imager can be used in the path of the therapy beam after the treated anatomy. Also, optical cameras can be used to image the profile or surface contour of the patient.

In a radiation therapy and/or diagnostic system including the self-shielding system according to the present invention, the rotational movement combined with an ionizing radiation imaging source and detector can be used to generate plane orthogonal x-rays, cone beam CT, a sparse data set for tomosynthesis, or digitally reconstructed radiographs to assist in anatomical positioning. The position of the anatomy with respect to the radiation beam size, shape, and position can be adjusted to locate the therapy beam in the desired position with respect to the anatomy. Alternatively, the radiation beam size, shape, and or position can be adjusted with respect to the anatomy to provide alignment for the planned treatment.

In a radiation therapy and/or diagnostic system including the self-shielding system according to the present invention, the rotational movement of the patient positioner or the beam in conjunction with the radiation source and a multi-leaf collimator or other beam modulation device can be used to deliver a highly optimized, pre-planned dose distribution to the treatment volume.

In one aspect of the invention, the gravity assist of a prone patient position and an optional anatomy fixation device maximize the separation of the target volume with respect to critical structures and other areas not intended to receive radiation.

According to the invention, by making the patient support table from a shielding material such as lead, and extending the beam block to surround the radiation source(s) entirely, the system can be made to include further self-shielding. General purpose radiation therapy machines that use higher energy beams for treating deep targets in the abdomen, for example, operate at energies up to and sometimes exceeding 21 MeV. This requires extensive shielding as the primary beam is very penetrating. Above 8 MeV, an x-ray beam produces neutrons which require additional thick shielding. A typical concrete bunker for a LINAC has walls on the order of 5-9 feet thick, leading to substantial construction costs and a large installation footprint. A self-shielded machine according to the invention can be installed in a room with minimal or no shielding, such as employed for CT or diagnostic x-ray rooms. This approach reduces the cost of installation substantially and also makes mobile operation feasible, bringing standard-of-care treatment options to smaller hospitals and rural areas with a low population density.

The self-shielded radiation therapy system according to the present invention can include shielding for the primary and scattered radiation such that the leakage radiation is below 0.02 mSv/week at the operator's location for a workload of 1000 Gy/week at isocenter when using the methods contained in National Council on Radiation Protection and Measurements (NCRP) report 151, hereby incorporated by reference in its entirety, for calculating and measuring the external dose rate. This very low exposure rate corresponds to the accepted level of radiation exposure for uncontrolled areas.

The self-shielded radiation therapy system can include full shielding for the primary and scattered radiation such that the leakage radiation is below 0.1 mSv/week at 1 meter from isocenter for a workload of 1000 Gy/week at isocenter when using the methods contained in NCRP report 151 for calculating and measuring the external dose rate. This low exposure rate corresponds to the accepted level of radiation exposure for controlled areas.

A highly shielded zone is produced for at least an area adjacent to the machine sufficient to house an operator console.

In one system to which the invention is applicable, the radiation source is a linear accelerator. In this configuration, the self-shielded radiation therapy system can include full shielding for the primary and scattered radiation such that the leakage radiation is below 0.02 mSv/week at 2 meters from the surface of the machine for a workload of 1000 Gy/week at isocenter when using the methods contained in NCRP report 151 for calculating and measuring the external dose rate. In this configuration, the self-shielded radiation therapy system can include shielding for the primary and patient scattered radiation such that the leakage radiation at the operator's location is below 0.1 mSv/week at 2 meters from the surface of the machine for a workload of 1000 Gy/week at isocenter when using the methods contained in NCRP report 151 for calculating and measuring the external dose rate. In this embodiment, the self-shielded radiation therapy system of the invention includes primary shielding which is better than 0.001% of the primary beam dose rate. This configuration corresponds to a level of shielding about ten times better than required for regulatory compliance.

The self-shielded radiation therapy system may include in-room shielding for an operator.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A shielding system for a radiation therapy system, comprising:
   a radiation source positioned within a source shield and configured to deliver a therapeutic radiation to a patient;
   a scatter shield configured to absorb scattered therapeutic radiation from the patient; the source shield coupled to the scatter shield and configured to absorb unwanted therapeutic radiation from the radiation source; and
   an anti-reflective beam dump coupled to the scatter shield and configured to absorb therapeutic radiation that is transmitted through the patient.

2. The shielding system according to claim 1, wherein thickness of shielding material used for the scatter shield, the source shield and the anti-reflective beam dump is selected such that leakage radiation is below 0.02 mSv/week at 2 meters from the surface of the radiation therapy system for a workload of 1000 Gy/week at isocenter.

3. The shielding system according to claim 1, wherein the radiation source is a linear accelerator.

4. The shielding system according to claim 1, wherein the the anti-reflective beam dump is positioned to absorb the beam transmitted through the patient and to reduce backscatter onto the patient.

5. The shielding system of claim 1, wherein the radiation source is configured to rotate around the patient.

6. The shielding system of claim 5 further comprising a table positioned within the scatter shield, the table having an aperture configured to permit passage of the patient's anatomy.

7. The shielding system of claim 6, wherein the patient's anatomy is a breast.

8. The shielding system of claim 1, wherein the therapeutic dose is configured for a cancer treatment.

9. The shielding system of claim 1, wherein the radiation source emits a programmable beam through a beam modulator.

10. The shielding system of claim 1, wherein the radiation source rotates about a vertical axis and moves along a horizontal axis.

11. The shielding system of claim 1, further comprising a high energy portal imager positioned in the path of the therapeutic radiation beam after the patient.

12. The shielding system of claim 1, further comprising an imaging system using ionizing radiation configured to image at least one portion of the patient anatomy.

13. The shielding system of claim 1, further comprising optical cameras configured to image at least one of a profile or surface contour of the patient.

14. The shielding system of claim 6, wherein the table is made from a shielding material.

15. The shielding system of claim 1, further comprising a high energy portal imager positioned in the path of the therapeutic radiation beam after the patient.

16. A shielding system for a radiation therapy system, comprising:
   a linear accelerator positioned within a lead source shield and configured to deliver a therapeutic radiation to a patient, wherein the linear accelerator is configured to rotate around the patient;
   a lead scatter shield configured to absorb scattered therapeutic radiation from the patient, wherein thickness of the scatter shield is selected such that leakage radiation is below 0.02 mSv/week at 2 meters from the surface of the radiation therapy system for a workload of 1000 Gy/week at isocenter;
   the lead source shield coupled to the scatter shield and configured to absorb unwanted therapeutic radiation from a the radiation source;
   an anti-reflective beam dump coupled to the scatter shield and configured to absorb therapeutic radiation that is transmitted through the patient and to reduce backscatter onto the patient; and,
   a table positioned within the scatter shield, the table having an aperture configured to permit passage of the patient's anatomy.

17. A method of treating cancer comprising:
   placing a patient on a table positioned within a scatter shield, the table having an aperture configured to permit passage of the patient's anatomy, the scatter shield configured to absorb scattered therapeutic radiation from the patient, wherein thickness of the scatter shield is selected such that leakage radiation is below 0.02 mSv/week at 2 meters from the surface of the radiation therapy system for a workload of 1000 Gy/week at isocenter and, wherein a first end of the scatter shield is coupled to the source shield and a second end of the scatter shield is coupled to an anti-reflective beam dump;
   configuring a beam of radiation through a beam modulator to deliver a dose of radiation to a target within the patient's anatomy;
   initiating the delivery of the dose of radiation to the target.

* * * * *